United States Patent
Sakamoto

(10) Patent No.: US 10,357,244 B2
(45) Date of Patent: Jul. 23, 2019

(54) SUTURING DEVICE

(71) Applicant: OLYMPUS CORPORATION, Tokyo (JP)

(72) Inventor: Tetsuyuki Sakamoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 186 days.

(21) Appl. No.: 15/701,519

(22) Filed: Sep. 12, 2017

(65) Prior Publication Data

US 2017/0367691 A1 Dec. 28, 2017

Related U.S. Application Data

(63) Continuation of application No. PCT/JP2015/079717, filed on Oct. 21, 2015.

(30) Foreign Application Priority Data

Mar. 18, 2015 (JP) ................... 2015-054560

(51) Int. Cl.
A61B 17/04 (2006.01)
A61B 17/062 (2006.01)
(Continued)

(52) U.S. Cl.
CPC ...... A61B 17/0469 (2013.01); A61B 17/0625 (2013.01); A61B 17/0491 (2013.01);
(Continued)

(58) Field of Classification Search
CPC ............ A61B 17/0469; A61B 17/0491; A61B 17/0625; A61B 17/0482;
(Continued)

(56) References Cited

U.S. PATENT DOCUMENTS 5,674,230 A * 10/1997 Tovey ................ A61B 17/0469
606/139
5,690,653 A 11/1997 Richardson et al.
(Continued)

FOREIGN PATENT DOCUMENTS

EP 2 889 008 A1 7/2015
JP 2001-500765 A 1/2001
(Continued)

OTHER PUBLICATIONS

Extended Supplementary European Search Report dated Dec. 19, 2018 in European Patent Application No. 15 88 5556.9.
(Continued)

Primary Examiner — Jocelin C Tanner
(74) Attorney, Agent, or Firm — Scully, Scott, Murphy & Presser, P.C.

(57) ABSTRACT

A suturing device includes a longitudinal axis member, an operation unit, a grasp portion, a suture needle, a first engaging member, a second engaging member, a first linear member connected to the first engaging member and the operation unit and configured to switch the first engaging member and the engaging portion into an engaged state or a disengaged state, and a second linear member connected to the second engaging member and the operation unit and configured to switch the second engaging member and the engaging portion into an engaged state or a disengaged state, wherein the first and the second linear member intersect a central axis of the longitudinal axis member between the grasp portion and a distal end of the longitudinal axis member and are inserted into an insertion path to be connected to the operation unit.

9 Claims, 10 Drawing Sheets

(51) Int. Cl.
  *A61B 17/00* (2006.01)
  *A61B 17/06* (2006.01)
  *A61B 17/29* (2006.01)
(52) U.S. Cl.
  CPC . *A61B 2017/0034* (2013.01); *A61B 2017/047* (2013.01); *A61B 2017/06028* (2013.01); *A61B 2017/06047* (2013.01); *A61B 2017/2932* (2013.01)
(58) Field of Classification Search
  CPC ...... A61B 2017/0034; A61B 2017/047; A61B 2017/06028; A61B 2017/06047; A61B 2017/2932; A61B 2017/06142
  See application file for complete search history.

(56) References Cited

U.S. PATENT DOCUMENTS

| | | |
|---|---|---|
| 5,693,071 A | 12/1997 | Gorecki et al. |
| 5,814,054 A * | 9/1998 | Kortenbach ....... A61B 17/0469 606/139 |
| 5,993,466 A | 11/1999 | Yoon |
| 8,496,674 B2 * | 7/2013 | Cabrera ................. A61B 17/04 606/144 |
| 2009/0312773 A1 | 12/2009 | Cabrera et al. |
| 2013/0317291 A1 | 11/2013 | Yamamoto |

FOREIGN PATENT DOCUMENTS

| | | |
|---|---|---|
| JP | 2010-005386 A | 1/2010 |
| JP | 2010-505525 A | 2/2010 |
| JP | 2010-142279 A | 7/2010 |
| JP | 2014-030544 A | 2/2014 |
| WO | WO 98/11829 A1 | 3/1998 |
| WO | WO 2008/045394 A2 | 4/2008 |
| WO | 2014/030544 A1 | 2/2014 |

OTHER PUBLICATIONS

International Search Report dated Jan. 12, 2016 issued in PCT/JP2015/079717.

* cited by examiner

SUTURING DEVICE

The present application is a Continuation of International Patent Application No. PCT/JP2015/079717, filed Oct. 21, 2015, claiming priority on Japanese Patent Application No. 2015-054560, filed Mar. 18, 2015, the contents of said Japanese Patent Application and said PCT Application being incorporated herein.

BACKGROUND OF THE INVENTION

Field of the Invention

The present invention relates to a suturing device.

Description of Related Art

Conventionally, a suturing device inserted into a body for suturing a tissue is known.

In Published Japanese Translation No. 2001-500765 of the PCT International Publication and Published Japanese Translation No. 2014-030544 of the PCT International Publication, a pair of grasp members which is capable of being opened and closed, a suture needle to which a suture thread is attached and sutures the tissue, and a transfer mechanism which transfers the suture needle between the pair of grasp members are provided, for example. In this suturing device, in a state in which the suture needle is engaged with one of the grasp members, the tissue is grasped by the pair of grasp members and the tissue is pierced with the suture needle. Next, the suture needle is transferred to the other grasp member by the transfer mechanism so that the suture thread penetrates the tissue. In the suturing device disclosed in Published Japanese Translation No. 2014-030544 of the PCT International Publication, since an operation of transferring the suture needle between the grasp members is repeatedly performed, continuous suturing is possible.

SUMMARY OF THE INVENTION

A suturing device according to a first aspect of the present invention includes a longitudinal axis member in which an insertion path extending in a longitudinal direction from a proximal end portion to a distal end portion is formed; an operation unit provided on a proximal end portion side of the longitudinal axis member; a grasp portion provided on a distal end portion side of the longitudinal axis member and configured to be capable of performing an opening and closing motion of a pair of grasp members by using an opening-closing operation member, the pair of grasp members including a first grasp member and a second grasp member; a suture needle having an engaging portion engageable with the pair of grasp members; a first engaging member provided in the first grasp member and configured to engage the suture needle with the first grasp member by engaging with the engaging portion; a second engaging member provided in the second grasp member and configured to engage the suture needle with the second grasp member by engaging with the engaging portion; a first linear member connected to the first engaging member and the operation unit and configured to switch the first engaging member and the engaging portion into an engaged state or a disengaged state by moving in the longitudinal direction; and a second linear member connected to the second engaging member and the operation unit and configured to switch the second engaging member and the engaging portion into an engaged state or a disengaged state by moving in the longitudinal direction, wherein the first linear member and the second linear member are inserted into the insertion path in a state in which the first linear member and the second linear member intersect a central axis of the longitudinal axis member at a proximal side with respect to a rotating shaft portion of the pair of grasp members.

As a second aspect of the present invention, in the suturing device according to the first or the second aspect, the first engaging member may be provided in the first grasp member to be slidable along a surface facing the second grasp members, the second engaging member may be provided in the second grasp member to be slidable along facing a surface facing the first grasp members, and the first engaging member and the second engaging member may respectively slide with respect to the first grasp member and the second grasp member by advancing and retracting the first linear member and the second linear member, thereby one of the first engaging member and the second engaging member may be engaged with the engaging portion and the suture needle may be held by one of the pair of grasp members corresponding to an engaging member engaged with the engaging portion.

As a third aspect of the present invention, in the suturing device according to the second aspect, the first engaging member and the second engaging member may be configured to be engaged with the engaging portion by sliding toward each proximal side of the grasp members.

As a fourth aspect of the present invention, the suturing device according to the first aspect may further include a cover member which fixes a rotating shaft portion of the pair of grasp members to the longitudinal axis member; and a pair of link members in which a distal end side thereof is connected to the rotating shaft portion and a proximal end side thereof is connected to a distal end portion of the opening-closing operation member, wherein the pair of grasp members may open and close via the link members by advancing and retracting the opening-closing operation member with respect to the longitudinal axis member; and the first linear member and the second linear member may pass between the pair of link members and intersect with each other on the proximal side with respect to the rotating shaft portion.

As a fifth aspect of the present invention, in the suturing device according to the fourth aspect, in a state in which the pair of grasp members are closed, the first linear member and the second linear member may come into contact with the rotating shaft portion such that the first linear member and the second linear member is spaced apart with respect to the central axis and an intersecting position of the first linear member and the second linear member in the longitudinal direction is restricted to be on a proximal side with respect to the rotating shaft portion.

As a sixth aspect of the present invention, in the suturing device according to the fourth or the fifth aspect, the first linear member and the second linear member may intersect between the rotating shaft portion of the pair of grasp members and a link rotating shaft portion of the link members in the longitudinal direction; and in a state in which the pair of grasp members are opened, the first linear member and the second linear member may come into contact with the link rotating shaft portion such that a curved position is restricted.

As a seventh aspect of the present invention, in the suturing device according to the fourth aspect, the link members may include a first joint pin which connects the first grasp member with the longitudinal axis member; and a second joint pin provided to be spaced apart from the first joint pin on a same axis as the first joint pin and configured to connect the second grasp member with the longitudinal axis member, wherein the first linear member and the second linear member may be inserted into a distal end portion of the longitudinal axis member through a gap between the first joint pin and the second joint pin.

As an eighth aspect of the present invention, in the suturing device according to the first aspect, the first linear member and the second linear member may be provided to extend at positions spaced apart with the central axis interposed therebetween when viewed from an opening and closing direction of the pair of grasp members.

As a ninth aspect of the present invention, the suturing device according to the first aspect may further include a sheath into which the longitudinal axis member is inserted; and a switching mechanism disposed in the sheath with the longitudinal axis member, connected to the first linear member and the second linear member, and configured to alternatively switch the engaged state or the disengaged state of the engaging portion with the first engaging member and the second engaging member.

DETAILED DESCRIPTION OF THE INVENTION

First Embodiment

Figure 1:
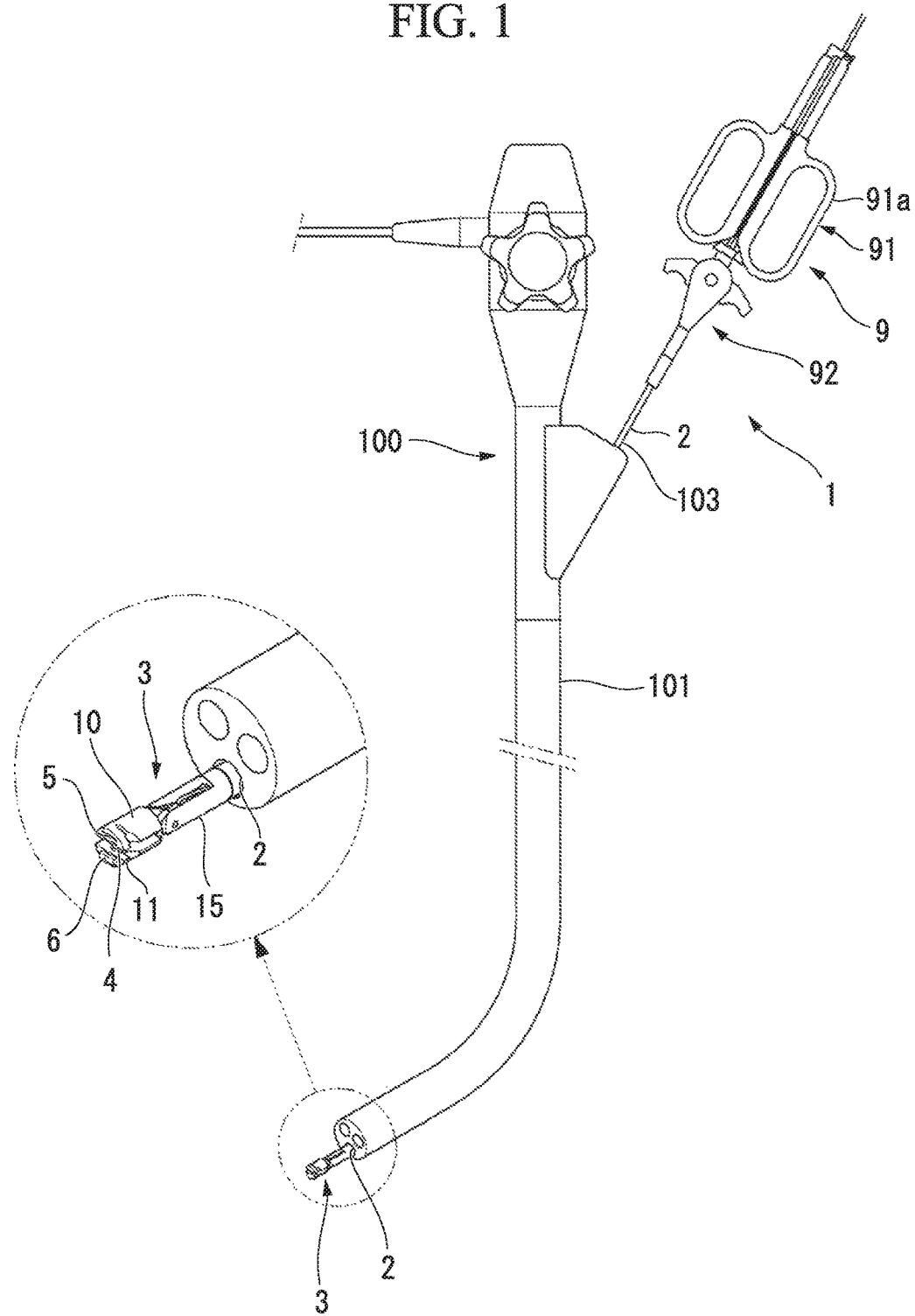
FIG. 1 is a general view illustrating a state in which a suturing device according to a first embodiment of the present invention is installed in an endoscope insertion portion.
Figure 2:
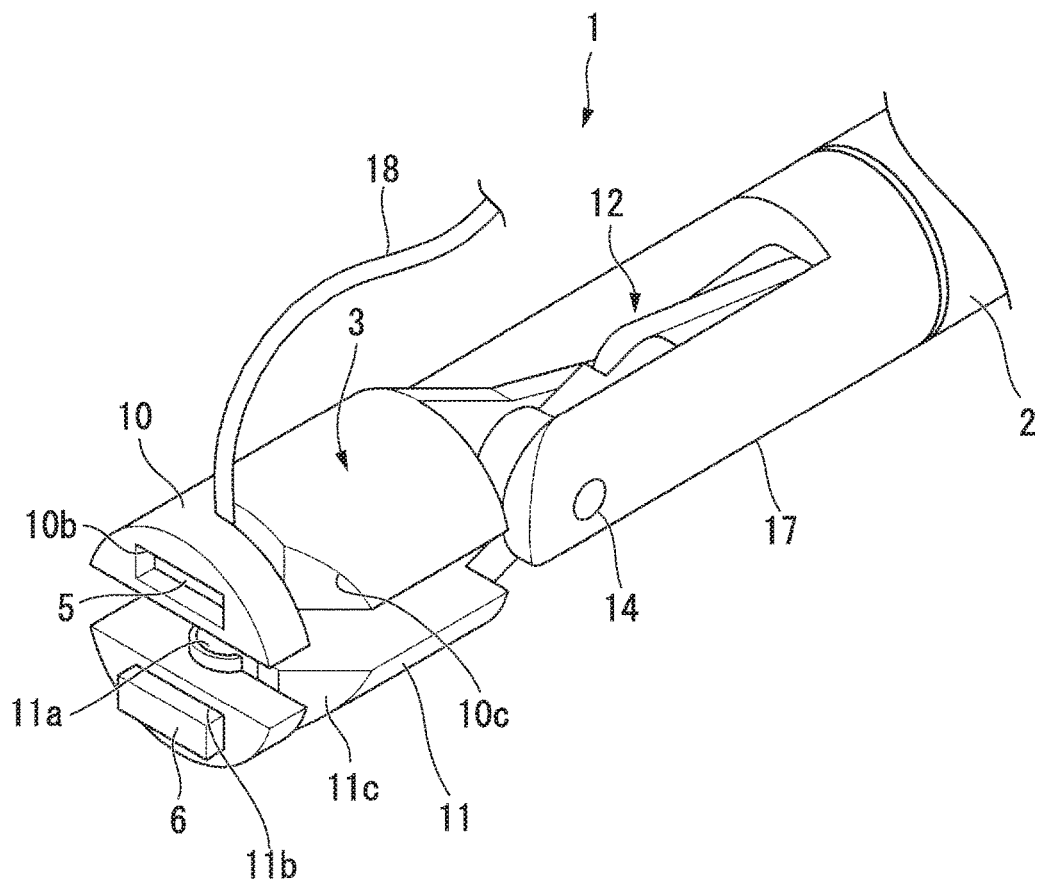
FIG. 2 is a perspective view illustrating a distal end portion of the suturing device according to the first embodiment of the present invention.
Figure 3:
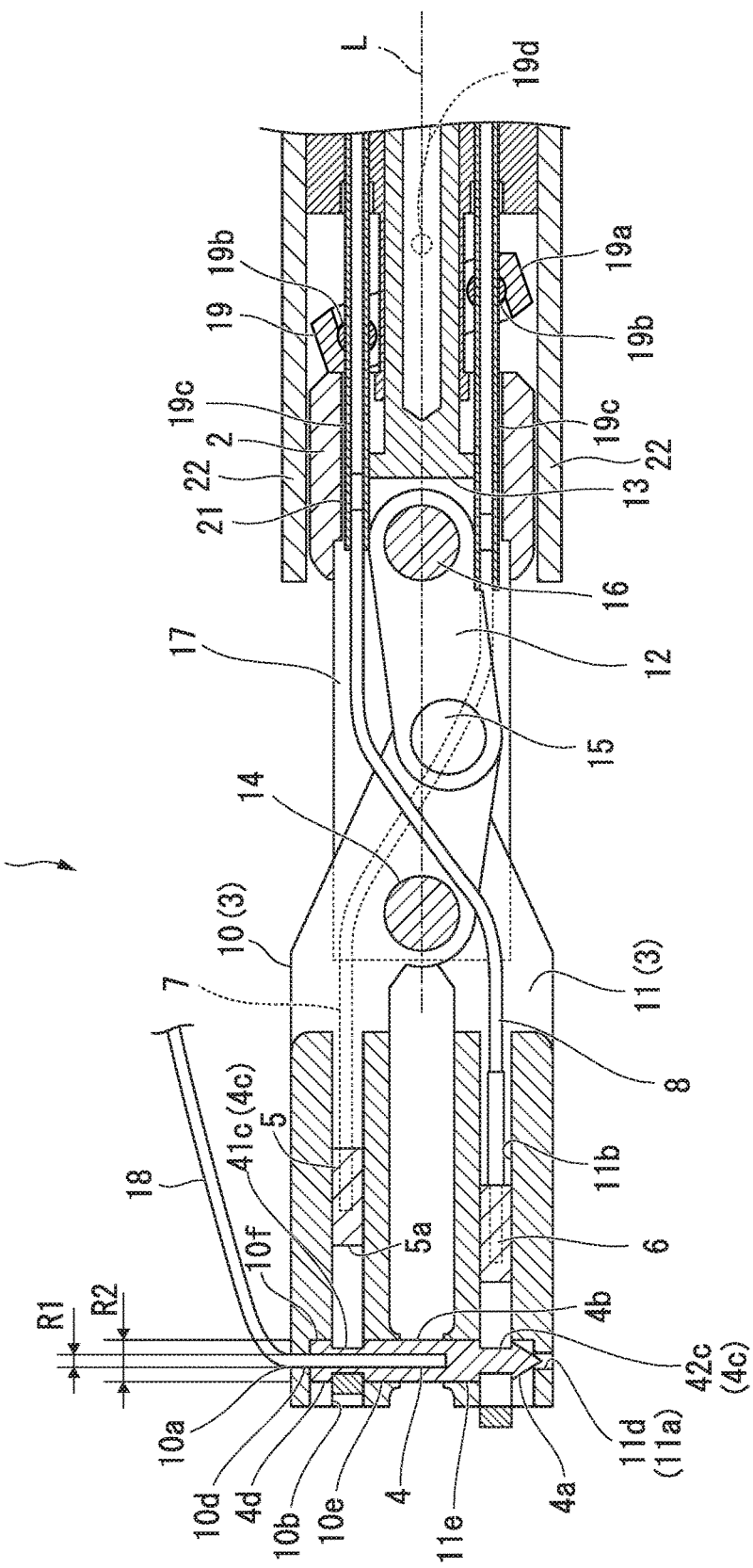
FIG. 3 is a view illustrating the distal end portion of the suturing device according to the first embodiment of the present invention and is a cross-sectional view in an opening and closing direction of a grasp portion on a central axis of a longitudinal axis member.
Figure 4:
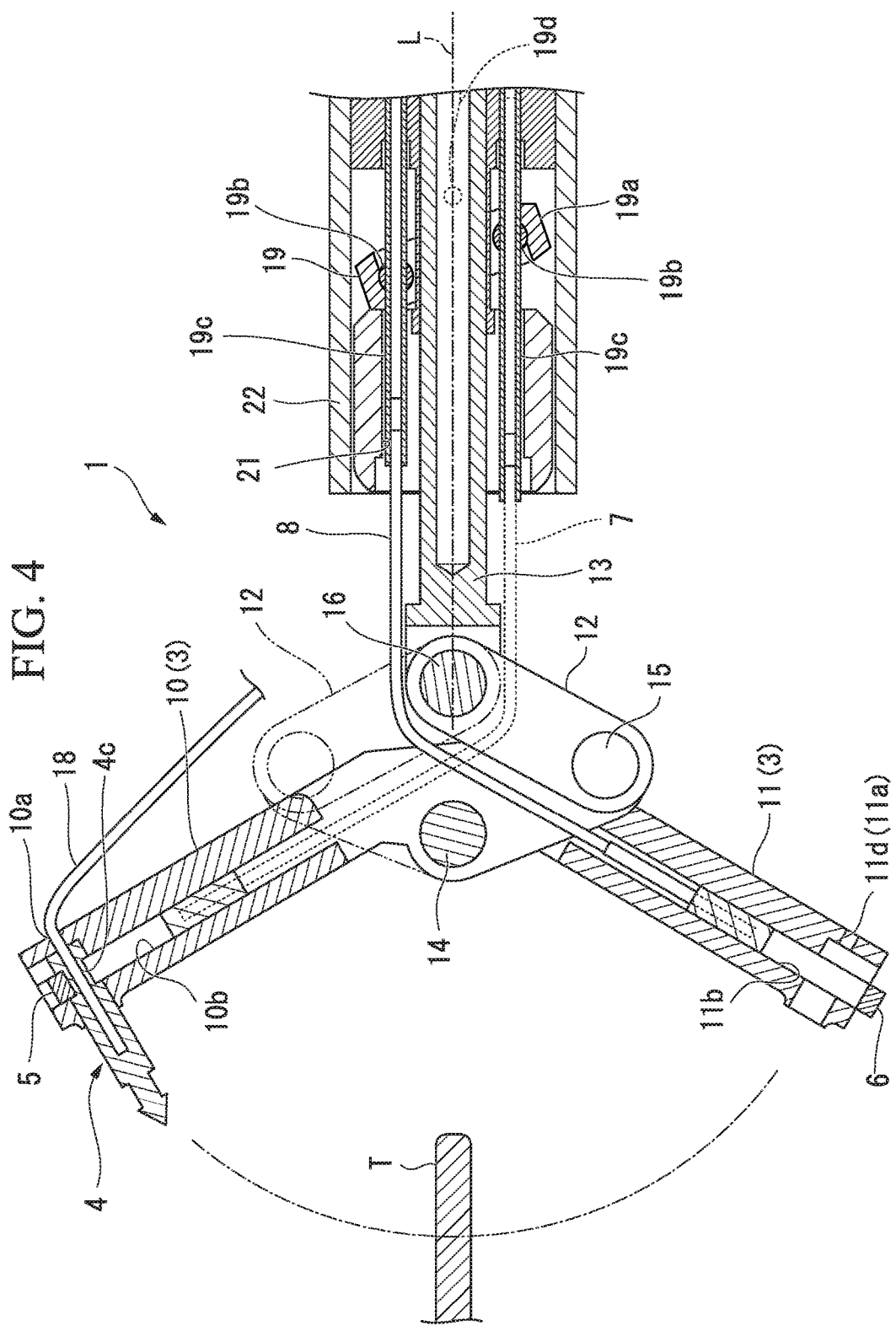
FIG. 4 is a view illustrating the distal end portion of the suturing device according to the first embodiment of the present invention and is a cross-sectional view in an opening and closing direction of a grasp portion on a central axis of a longitudinal axis member.

A suturing device 1 according to a first embodiment of the present invention will be described. FIG. 1 is a general view of the suturing device 1. FIG. 2 is a perspective view of the suturing device 1. FIGS. 3 and 4 are views illustrating the distal end portion of the suturing device 1 and are cross-sectional views in an opening and closing direction of a grasp portion 3 on a central axis L of a longitudinal axis member 2. FIG. 3 illustrates a state in which a pair of grasp members is closed, and FIG. 4 illustrates a state in which the pair of grasp members are opened.

As illustrated in FIG. 1, the suturing device 1 is used by being inserted into an endoscope insertion portion 101 of an endoscope 100 for suturing a living body tissue using a suture needle. As illustrated in FIGS. 1 to 4, the suturing device 1 includes a suture needle 4, the longitudinal axis member 2, the grasp portion 3, a first engaging member 5, a second engaging member 6, a first linear member 7, a second linear member 8 (see FIG. 3), and an operation unit 9.

The longitudinal axis member 2 is a member having flexibility and extending in a longitudinal direction from a proximal end to a distal end along the central axis L. The longitudinal axis member 2 has an insertion path 21 (see FIG. 3) formed therein. The operation unit 9 is provided at the proximal end of the longitudinal axis member 2, and the grasp portion 3 is provided at a distal end side of the longitudinal axis member. An opening-closing operation member 13 is inserted into the insertion path 21 of the longitudinal axis member 2 to be advanced and retracted. The longitudinal axis member 2 is inserted through a sheath 22.

In the grasp portion 3, as illustrated in FIGS. 2 and 3, the pair of grasp members including a first grasp member 10 and a second grasp member 11 are connected to the opening-closing operation member 13 via a link member 12. In the grasp portion 3, the first grasp member 10 and the second grasp member 11 are connected to be relatively rotatable by a support pin (a rotating shaft portion) 14. A distal end portion of the link member 12 is connected to proximal ends of the first grasp member 10 and the second grasp member 11 so as to be rotatable about a distal end side joint pin 15. A proximal end portion of the link member 12 is connected to the distal end portion of the opening-closing operation member 13 so as to be rotatable about a proximal end side joint pin (a link rotating shaft portion) 16. A cover member 17 is provided at a distal end of the longitudinal axis member 2. The support pin 14 is connected to a distal end portion of the cover member 17, and the first grasp member 10 and the second grasp member 11 are rotatably supported by the cover member 17.

When the opening-closing operation member 13 is pulled in the insertion path 21, the pair of grasp members 10 and 11 is closed to be substantially parallel along the central axis L as illustrated in FIG. 3. As illustrated in FIG. 4, when the opening-closing operation member 13 is pushed out from the insertion path 21, the first grasp member 10 and the second grasp member 11 rotate in conjunction with the link member 12 and relatively rotate about the support pin 14 to be in an opened state.

Figure 5:
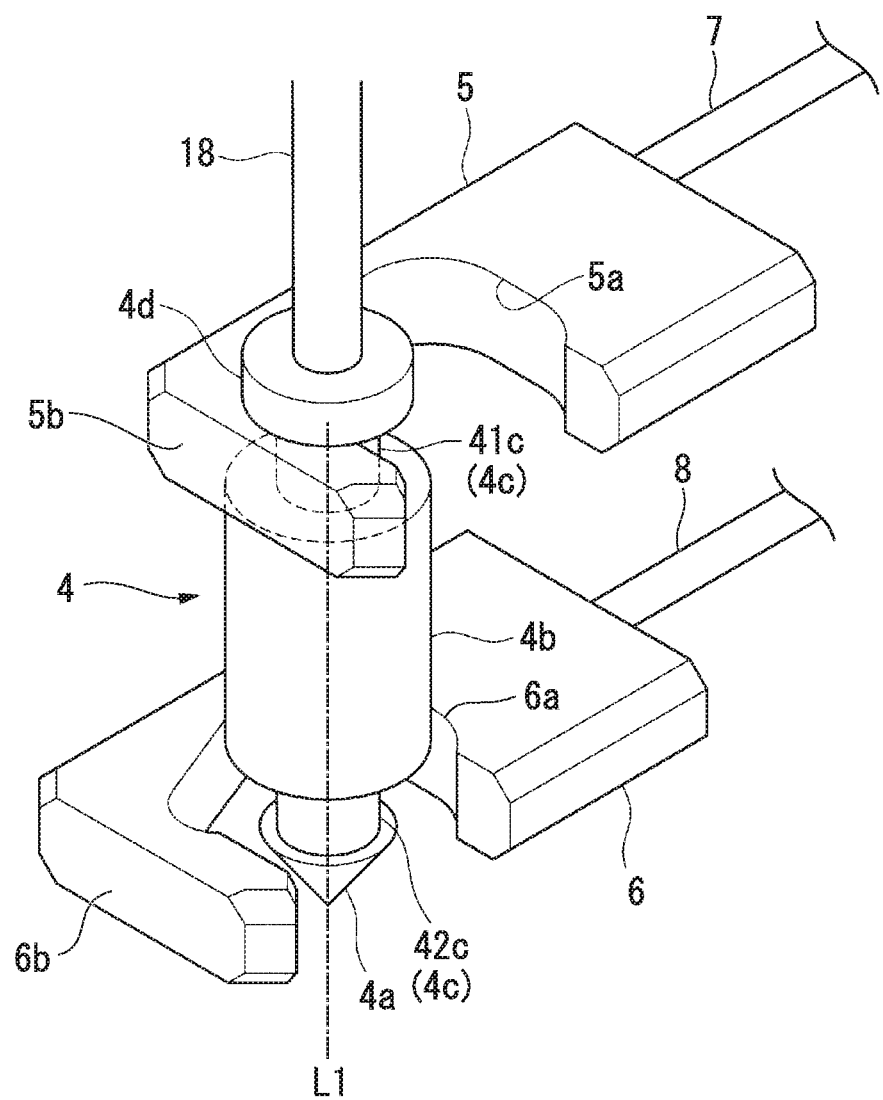
FIG. 5 is a perspective view schematically illustrating a positional correlation between a suture needle, a first engaging member, and a second engaging member in the suturing device according to the first embodiment of the present invention.

The suture needle 4 has substantially a columnar shape. As illustrated in FIG. 5, the suture needle 4 has a main body portion 4b having the largest outer diameter dimension at a central portion in a longitudinal direction L1 and has a conical pointed end portion 4a at one end portion (a distal end). A suture thread 18 is fixed to the other end (a proximal end) of the suture needle by adhesion or the like. The suture needle 4 has a flange portion 4d at a proximal end portion thereof. A small-diameter portion (an engaging portion) 4c, which has a diameter smaller than that of a maximum diameter of the pointed end portion 4a and a diameter of the flange portion 4d, is formed over the whole circumference of the main body portion 4b at both sides in the longitudinal direction L1 of the main body portion.

As illustrated in FIGS. 3 and 4, a lumen 10b is formed in the first grasp member 10 and the first engaging member 5 is accommodated in the lumen 10b so as to be slidable in a direction of the central axis L. Similarly, a lumen 11b is formed in the second grasp member 11 and the second engaging member 6 is accommodated in the lumen 11b so as to be slidable in the direction of the central axis L. Through-holes 10a and 11a passing through in the opening and closing direction of the pair of grasp members 10 and 11 are respectively formed at distal ends of the first grasp member 10 and the second grasp member 11. The through-holes 10a and 11a communicate with the lumens 10b and 11b. As illustrated in FIG. 2, the through-holes 10a and 11a are formed to communicate with notches 10c and 11c formed at side end portions of the first grasp member 10 and the second grasp member 11.

As illustrated in FIG. 3, an opening width R1 of a small-diameter portion 10d on an outer surface side of the through-hole 10a of the first grasp member 10 is formed in a dimension slightly larger than that of the suture thread 18. The through-hole 10a has a large-diameter portion 10e formed through from a facing surface side with respect to the the second grasp member 11 to the lumen 10b. An opening width R2 of the large-diameter portion 10e has a slightly larger dimension than a diameter of the main body portion 4b of the suture needle 4. A step portion 10f is formed between the small-diameter portion 10d of the through-hole 10a and the lumen 10b. The step portion 10f has a dimension substantially equal to a dimension in an axial direction of the flange portion 4d of the suture needle 4. The step portion 10f is configured such that the flange portion 4d comes into contact with the step portion 10f when the suture needle 4 is held by the first grasp member 10.

The through-hole 11a of the second grasp member 11 also has the same configuration as the through-hole 10a of the first grasp member 10. When the suture needle 4 is engaged with the second grasp member 11 side, a distal end of the pointed end portion 4a of the suture needle 4 is stored in a small-diameter portion 11d of the through-hole 11a of the second grasp member 11.

Figure 6:
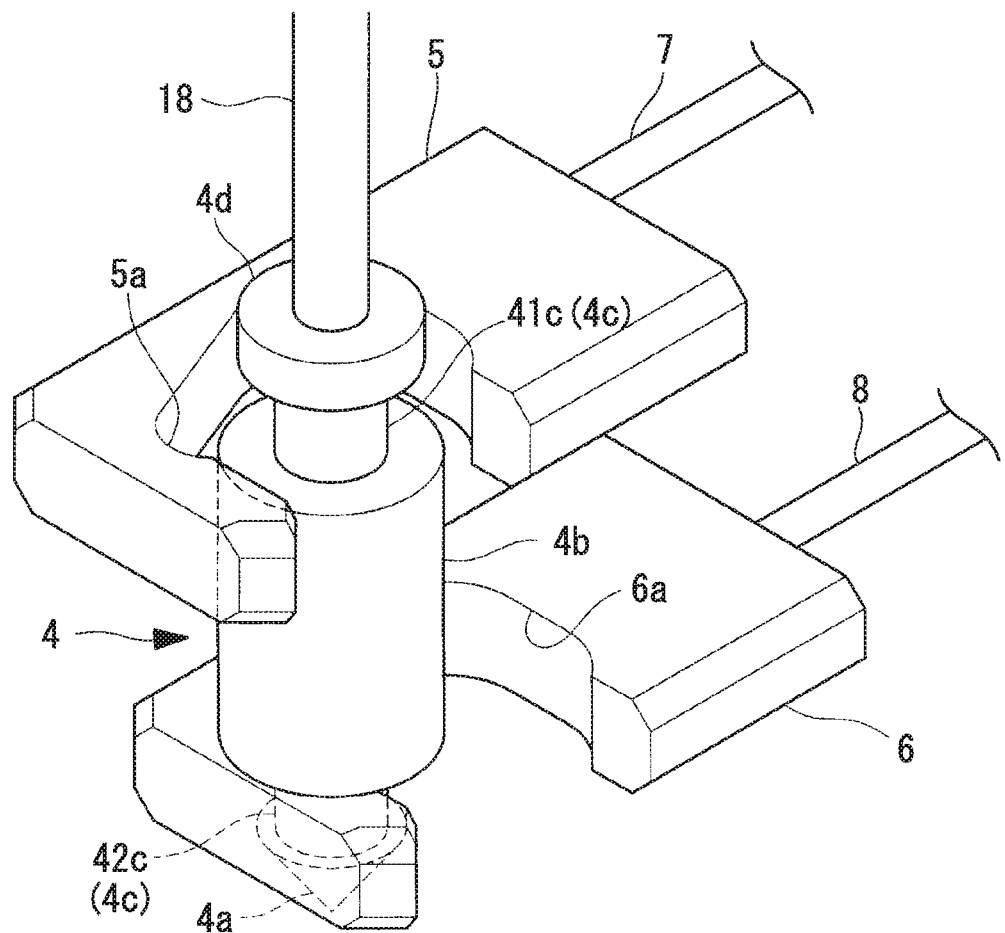
FIG. 6 is a perspective view schematically illustrating a positional correlation between the suture needle, the first engaging member, and the second engaging member in the suturing device according to the first embodiment of the present invention.

The first engaging member 5 is substantially a flat member provided in the first grasp member 10. The first engaging member 5 is provided inside the lumen 10b of the first grasp member 10 so as to be slidable along a surface facing the second grasp member 11 in the first grasp member 10. As illustrated in FIG. 5, the first engaging member 5 is formed by cutting a portion thereof out from an edge end portion in a direction along a sliding direction toward a center portion and has an opening 5a passing through in a thickness direction of the first engaging member. The first engaging member 5 is formed in a hook shape as a whole. A plate thickness of the first engaging member 5 is smaller than a length of a first small-diameter portion 41c in the longitudinal direction L1. As illustrated in FIG. 6, the opening 5a is formed to have a dimension through which the flange portion 4d and the pointed end portion 4a are capable of passing without being interfering with. The first engaging member 5 is capable of engaging the suture needle 4 with the first grasp member 10 by engaging an edge of the opening 5a with the first small-diameter portion 41c of the suture needle 4. A distal end of the first linear member 7 is fixed to a proximal end portion of the first engaging member 5 by adhesion or the like.

The second engaging member 6 has the same shape as the first engaging member 5. As with the first engaging member 5, the second engaging member 6 is slidably provided in the second grasp member 11. A distal end of the second linear member 8 is fixed to a proximal end portion of the second engaging member 6 by adhesion or the like. The first linear member 7 and the second linear member 8 are respectively connected to positions offset from centers of the proximal end portions of the first engaging member 5 and the second engaging member 6 in order to prevent mutual interference. The second linear member 8 is connected to the second engaging member 6 at a position offset from a center of the proximal end portion of the second engaging member 6 to a side opposite to a connection position between the first engaging member 5 and the first linear member 7 (see FIG. 7). As illustrated in FIG. 6, the second engaging member 6 is capable of engaging the suture needle 4 with the second grasp member 11 by engaging an edge of an opening 6a with a second small-diameter portion 42c of the suture needle 4.

The first linear member 7 and second linear member 8 (hereinafter, sometimes simply referred to as "linear members 7 and 8") are wires, for example. A distal end portion of the first linear member 7 is connected to the first engaging member 5 and a proximal end portion of the first linear member 7 is connected to the operation unit 9. Specifically, the linear members 7 and 8 are constituted by a single-wire having high rigidity from a portion exposed from the insertion path 21 to the distal end portion to facilitate pushing the first engaging member 5 and the second engaging member 6 (hereinafter, sometimes simply referred to as "engaging members 5 and 6"). Portions of the linear members 7 and 8 accommodated in the insertion path 21 are constituted by a stranded wire having less rigidity than that of the distal end portion in consideration of followability to curvature of the endoscope insertion portion 101 and the sheath 22. The first linear member 7 is capable of switching the first engaging member 5 and the first small-diameter portion 41c of the suture needle 4 to an engaged state or a disengaged state by advancing and retracting in the direction of the central axis L.

A distal end portion of the second linear member 8 is connected to the second engaging member 6 and a proximal end portion of the second linear member is connected to the operation unit 9. The second linear member 8 is capable of switching the second engaging member 6 and the second small-diameter portion 42c of the suture needle 4 to an engaged state or a disengaged state by advancing and retracting in the direction of the central axis L. The suture needle 4 is held by one of the pair of grasp members by engaging with either the first engaging member 5 or the second engaging member 6. The engagement between the suture needle 4 and the pair of grasp members will be described below.

As illustrated in FIGS. 3 and 4, the linear members 7 and 8 intersect the central axis L of the longitudinal axis member 2 between the grasp portion 3 and the distal end of the longitudinal axis member 2 when viewed from an axial direction of the support pin 14. The proximal end portions of the linear members 7 and 8 are inserted into the insertion path 21 and connected to the operation unit 9. When viewed from the axial direction of the support pin 14, the first linear member 7 and the second linear member 8 intersect on a proximal side with respect to the support pin 14 and their positional correlation with respect to the central axis L of the longitudinal axis member 2 is reversed.

Figure 7:
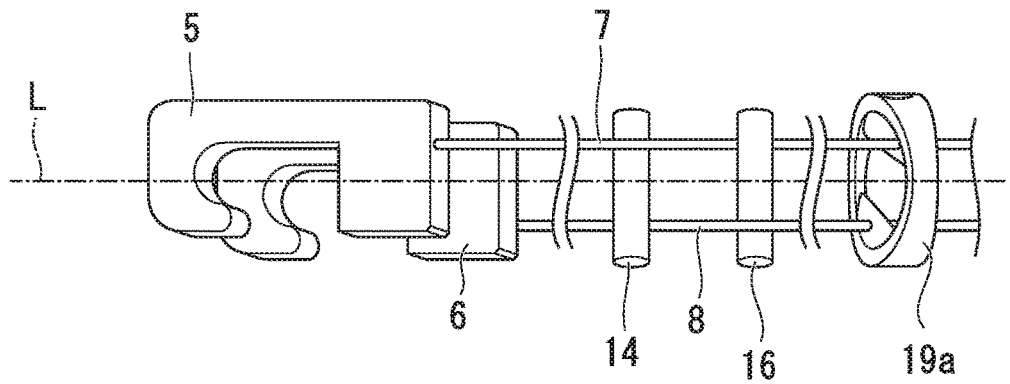
FIG. 7 is a schematic view illustrating a correlation between an engaging member, a linear member, a rotating shaft portion, a joint pin, and a ring member in the suturing device according to the first embodiment of the present invention.

FIG. 7 is a schematic view illustrating a correlation between the engaging members 5 and 6, the linear members 7 and 8, the support pin 14, the proximal end side joint pin 16, and a ring member 19a, of the suturing device 1. As illustrated in FIG. 7, the first linear member 7 and the second linear member 8 are provided to be spaced apart to extend substantially in parallel when viewed from the opening and closing direction of the pair of grasp members 10 and 11 (a direction perpendicular to an axis of the support pin 14). As a result, a transfer of a force of the linear members is prevented from being disturbed due to contact between the linear members. In addition, it is possible to prevent the linear members 7 and 8 from being worn due to the contact between the linear members 7 and 8 and prevent the linear members from being damaged.

In the present embodiment, the linear members 7 and 8 are inserted between a pair of link members 12, and the first linear member 7 and the second linear member 8 are intersected between the support pin 14 and the joint pin 15 when viewed from the axial direction of the support pin 14.

Figure 8:
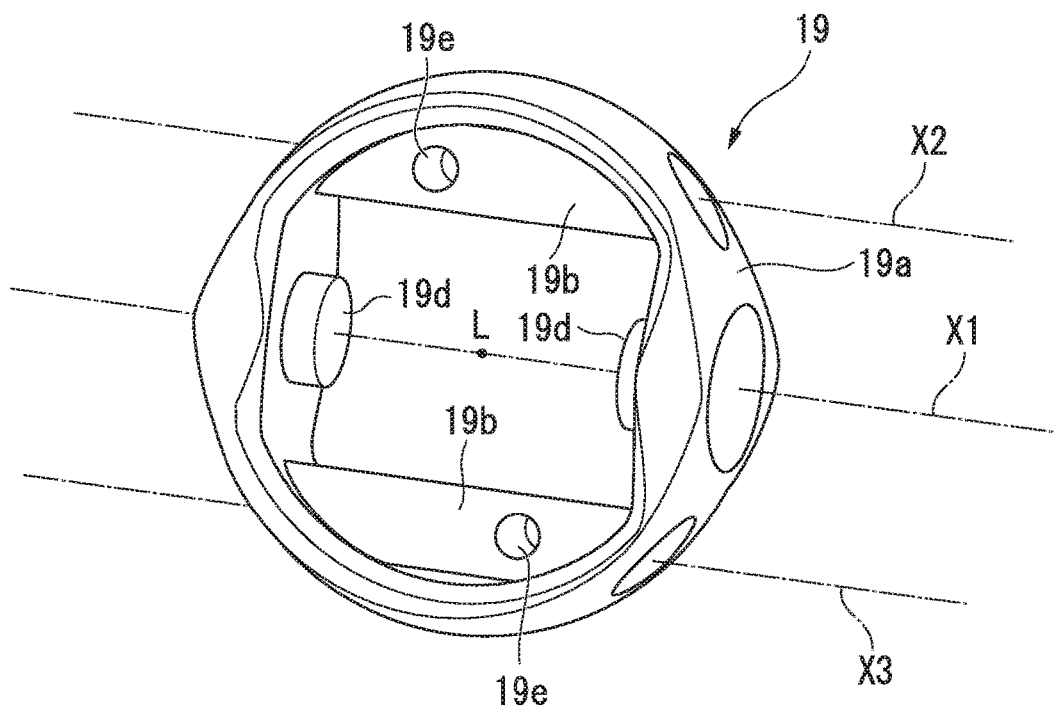
FIG. 8 is a perspective view illustrating a ring member in the suturing device according to the first embodiment of the present invention.

As illustrated in FIG. 4, a switching mechanism 19 which alternatively performs holding (an engaged state) or releasing (a disengaged state) of the suture needle 4 by the engaging members 5 and 6 is provided in the suturing device 1. As illustrated in FIG. 8, the switching mechanism 19 includes the ring member 19a and two columnar members 19b. The ring member 19a is formed in an annular shape and is provided so as to be swingable around a swinging axis X1 perpendicular to the central axis L of the longitudinal axis member 2 via rotating support portions 19d. The two columnar members 19b are provided on an inner circumferential portion of the ring member 19a to be arranged substantially in parallel on opposite sides of the swinging axis X1. The columnar members 19b are attached to the ring member 19a to be respectively rotatable around axes X2 and X3 parallel to the swinging axis X1. A through-hole 19e through which each of the linear members 7 and 8 is inserted is formed in each of the columnar members 19b. The central axis L of the longitudinal axis member 2 is positioned between the two through-holes 19e in a direction of the swinging axis X1. The through-holes 19e of the two columnar members 19b are formed at symmetrical positions with respect to the swinging axis X1. As a result, a state in which the linear members 7 and 8 inserted through the through-holes 19e are spaced apart from each other is capable of being maintained. As illustrated in FIGS. 3 and 4, a coil tube 19c is inserted and fixed to each of the through-holes 19e, and each of the linear members 7 and 8 is inserted and fixed to the coil tube 19c. The switching mechanism 19 is provided in the sheath 22.

The ring member 19a moves like a seesaw and alternatively switches between the holding and the releasing of the suture needle 4 by the engaging members 5 and 6 in accordance with a traction of either one of the first linear member 7 or the second linear member 8.

As illustrated in FIG. 1, the operation unit 9 is disposed on the proximal side of the longitudinal axis member 2 and includes an operation unit main body 90, an opening-closing operation unit 91 for performing an opening and closing operation of the pair of grasp members 10 and 11, and a transfer operation unit 92 for pulling the linear members 7 and 8.

The opening-closing operation unit 91 includes an opening-closing handle 91a and is configured to be capable of pushing and pulling the opening-closing operation member 13 (see FIG. 3) in the direction of the central axis L by an opening and closing operation of the opening-closing handle 91a.

Figure 9:
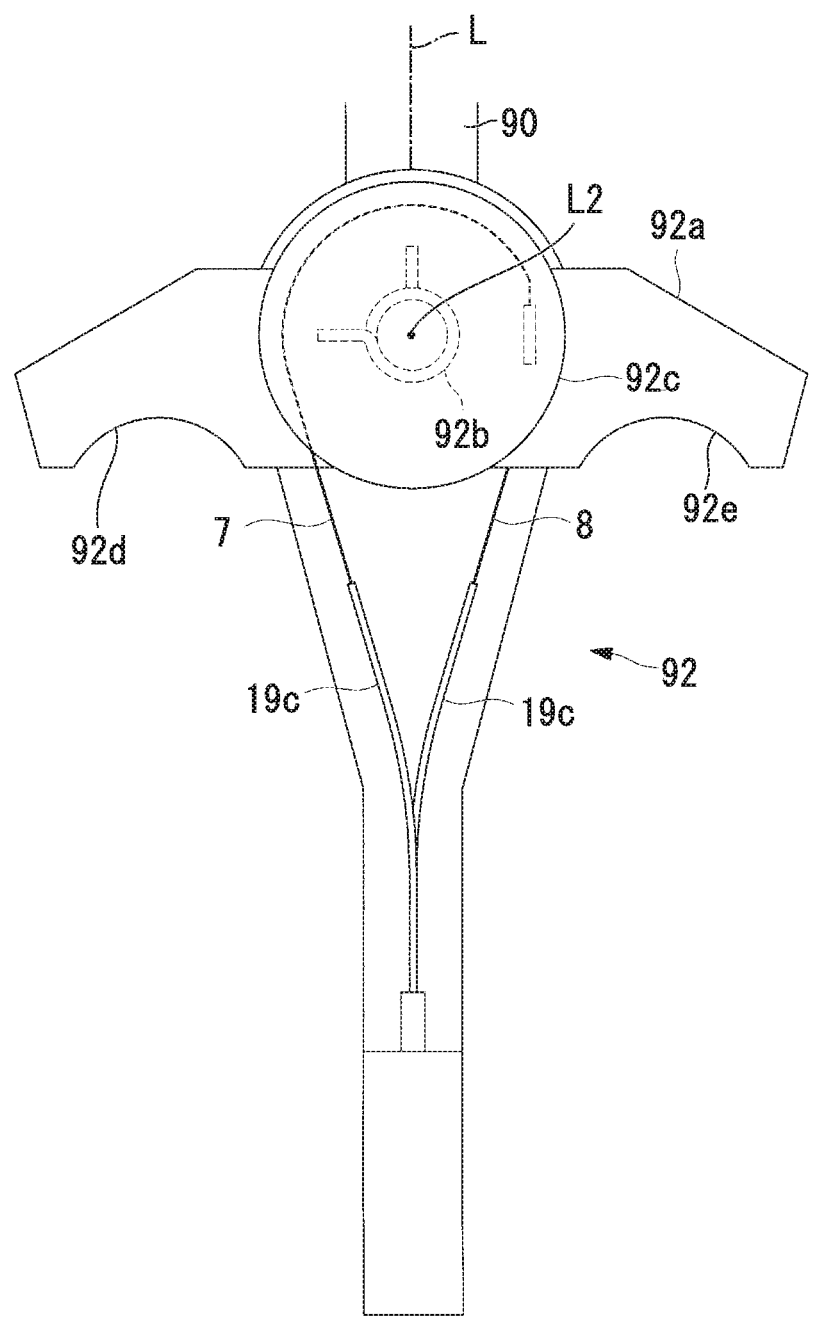
FIG. 9 is a plan view illustrating a transfer operation unit.
Figure 10:
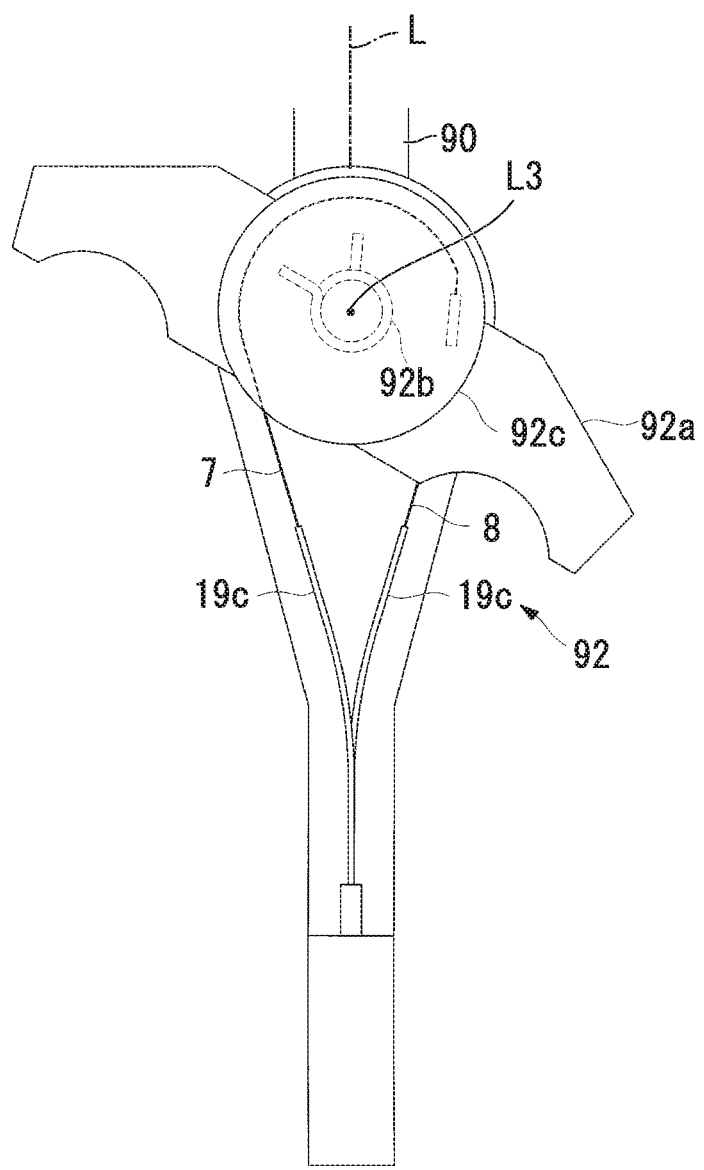
FIG. 10 is a plan view illustrating a transfer operation unit.

FIGS. 9 and 10 are plan views of the transfer operation unit 92 of the suturing device 1. The transfer operation unit 92 includes a handle 92a and two pulleys 92c. The handle 92a is provided in the operation unit main body 90 to be swingable around a swinging axis L2 perpendicular to the central axis L. The two pulleys 92c are disposed on opposite surfaces of the handle 92a so that the handle 92a is sandwiched in the swing axis L2 and rotatably attached to the handle 92a with a torsion spring 92b interposed therebetween. The first linear member 7 is wound around a first pulley 92c and an end portion thereof is fixed to the first pulley 92c. The second linear member 8 is wound around a second pulley (not shown) in a direction opposite to that of the first pulley 92c and an end portion thereof is fixed to the second pulley. On the handle 92a, finger hook portions 92d and 92e are formed at two positions on opposite sides of the central axis L.

An operation of the suturing device 1 according to the present embodiment will be described.

First, the suture needle 4 and the engaging members 5 and 6 are engaged. The engaging members 5 and 6 are respectively disposed in the lumens 10b and 11b such that hook portions 5b and 6b on the distal side with respect to the openings 5a and 6a are positioned on the distal side with respect to the through-holes 10a and 11a in the direction of the central axis L. An operator inserts the suture thread 18 from the notch 10c of the first grasp member 10. When the suture thread 18 is pulled toward the proximal side in a state in which the suture thread 18 inserted from the notch 10c is accommodated in the small-diameter portion 10d of the through-hole 10a, the flange portion 4d comes into contact with the step portion 10f of the first grasp member 10. In this state, the first small-diameter portion 41c is positioned in the lumen 10b, and an end portion of the main body portion 4b is positioned in the large-diameter portion 10e of the through-hole 10a of the first grasp member 10. Further, the first small-diameter portion 41c is positioned in the opening 5a of the first engaging member 5. When the first engaging member 5 is pulled toward the proximal side by pulling the handle 92a of the transfer operation unit 92 toward the proximal side, the hook portion 5b comes into contact with the first small-diameter portion 41c of the suture needle 4 and the suture needle 4 is engaged with the first engaging member 5. Since the suture needle 4 is pushed toward the proximal end side by the first engaging member 5 in a state in which the suture needle is in contact with the hook portion 5b, the step portion 10f, and the large-diameter portion 10e of the through-hole 10a, the suture needle 4 is engaged with the first grasp member 10 side and held.

Next, the opening-closing handle 91a of the opening-closing operation unit 91 is closed and the grasp portion 3 is held in a closed state. The suturing device 1 is inserted into the endoscope insertion portion 101 of the endoscope 100 inserted into the body through a forceps opening 103 and the suturing device 1 is caused to protrude from the distal end side of the endoscope insertion portion 101.

The operator brings the distal end portion of the suturing device 1 close to a target tissue on which a suturing treatment is performed. When the operator closes the opening-closing handle 91a after the grasp portion 3 in an opened state by opening the opening-closing handle 91a is brought into contact with the tissue, the grasp portion 3 is closed and the tissue is grasped. At this time, when the grasp portion 3 is operated to open and close in a state in which the first linear member 7 is pulled to the proximal side, a state in which the suture needle 4 is engaged with the first grasp member 10 is maintained. Although not illustrated, when the grasp portion 3 is closed and catches a tissue T, the pointed end portion 4a of the suture needle 4 pierces the tissue T to penetrate through the tissue T. In this state, the second small-diameter portion 42c on a distal end side of the suture needle 4 is in the lumen 11b of the second grasp member 11 and is positioned in the opening 6a of the second engaging member 6. When the operator pulls one finger hook portion 92e of the handle 92a of the transfer operation unit 92 toward the proximal side, the second linear member 8 is pulled to cause the hook portion 6b of the second engaging member 6 to be engaged with the second small-diameter portion 42c of the suture needle 4 and further to be pushed toward the proximal end side so that the suture needle 4 is held on the side of second grasp member 11.

At this time, the columnar member 19b fixed to the second linear member 8 correspondingly moves to the proximal end side according to a movement of the second linear member 8. Thereafter, the ring member 19a swings around the swinging axis X1 and the columnar members 19b through which the first linear member 7 is inserted moves toward the distal side to cause the first linear member 7 to move toward the distal side. As a result, the engaged state between the first engaging member 5 and the suture needle 4 is released.

After the grasp portion 3 is released from the tissue T by opening the opening-closing handle 91a, when the operator closes the opening-closing handle 91a again and pulls the finger hook portion 92d of the transfer operation unit 92 toward the proximal side, the first linear member 7 moves toward the proximal side and the suture needle 4 and the first engaging member 5 are engaged. In the switching mechanism 19, the second engaging member 6 is moved toward the distal side to release the engagement between the suture needle 4 and the second engaging member 6 by a motion reverse to that in a case in which the above-described second linear member 8 moves toward the proximal side. By repeating this operation, the suture needle 4 is transferred between the first grasp member 10 and the second grasp member 11 and thereby the tissue T is sutured. At this time, since the notch 10c of the first grasp member 10 is formed at a position that is capable of being recognized within view of the endoscope 100, the operator is capable of recognizing the state in which the suture thread 18 is inserted into the notch 10c.

In a case in which a curved portion of the longitudinal axis member 2 is curved, slack may occur in the linear members 7 and 8. A resilient force generated by elastic deformation of the torsion spring 92b applies tension that is large enough to eliminate the slack generated in the linear members 7 and 8 according to a posture of the curved portion of the longitudinal axis member 2. This tension is transmitted to the engaging members 5 and 6 connected with the linear members 7 and 8, and the suture needle 4 is held by the engaging members 5 and 6. Thereby, in the suturing device 1, the tension is constantly applied to the suture needle 4 even in a state in which the curved portion is curved, and it is possible to prevent the suture needle 4 from falling off during the manipulation.

At the time of the above-described operation, according to the present embodiment, the linear members 7 and 8 performing the movement operation are not easily affected by the opening and closing operation of the grasp portion 3 and the suturing treatment is capable of being stably performed. Features of the suturing device 1 of the present application will be described while comparing with a conventional example.

Figure 12:
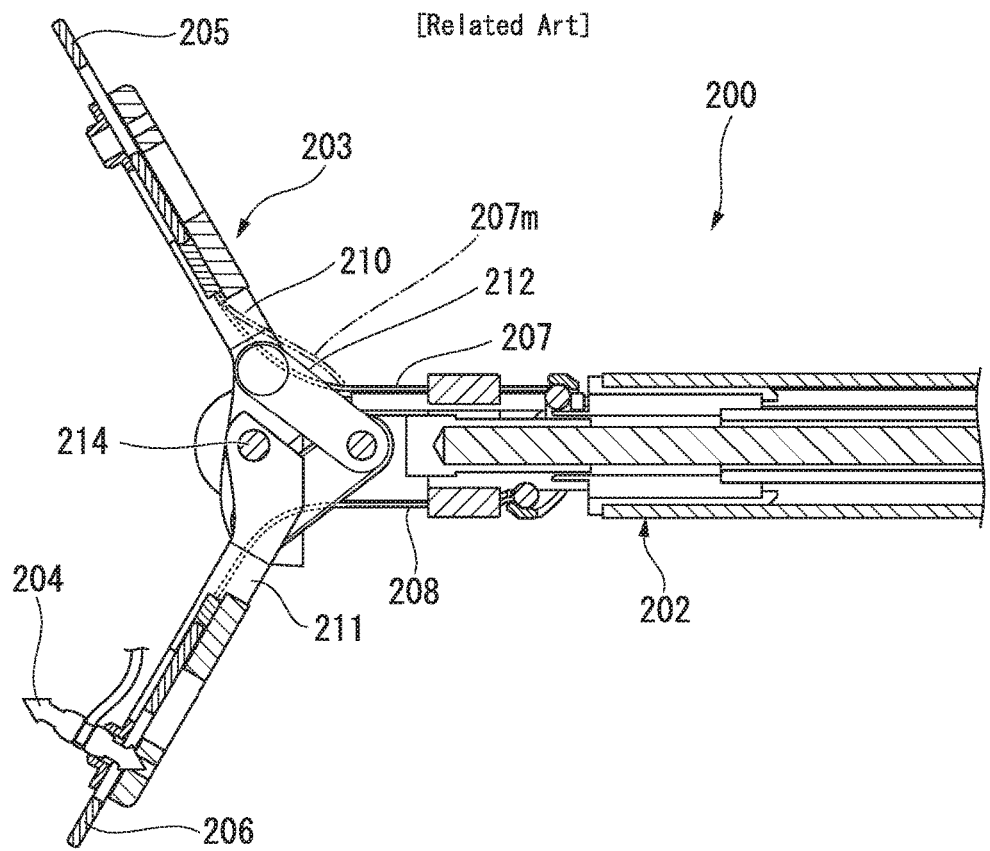
FIG. 12 is a view illustrating a conventional suturing device and is a cross-sectional view passing through a central axis of a longitudinal axis member in an opening and closing direction of a grasp portion.

FIG. 12 is a view illustrating an example of a conventional suturing device 200. As illustrated in FIG. 12, in the conventional suturing device 200, a first linear member 207 connected to a first engaging member 205 and a second linear member 208 connected to a second engaging member 206 are respectively connected in parallel with an axis of a longitudinal axis member 202 over the entire longitudinal direction. Therefore, in a state in which a grasp portion 203 is closed, the linear members 207 and 208 extend linearly. In a motion in which the grasp portion 203 is widely opened from its closed state, the linear members 207 and 208 (transfer wires) change from a linear state to a curved state according to the opening motion of the grasp portion. At this time, since a change in curvature of the curves of the first linear member 207 and the second linear member 208 (the transfer wires) is large in the vicinity of a rotating shaft (a pin) of grasp members 210 and 211, buckling may occur in the curved portions of the linear members 207 and 208 (the transfer wires). In addition, since the linear members 207 and 208 have higher rigidity at a portion connected to the engaging members 205 and 206 than at a portion positioned in the longitudinal axis member 202, the linear members 207 and 208 may not be smoothly curved due to the rigidity of the linear members 207 and 208 themselves depending on an opening motion of the grasp portion 203. As a result, as illustrated in FIG. 12, when a pair of grasp members 210 and 211 are widely opened, the linear members 207 and 208 are moved in an outer side direction away from a support pin 214 (a position indicated by a chain line 207m in FIG. 12, for example) due to their own rigidity.

As described above, when the linear members 207 and 208 are moved to the outer sides, a path of the linear member 207 between a proximal end portion of the grasp portion 203 and a distal end portion of the longitudinal axis member 202 changes greatly. As a result, the first engaging member 205 is pushed toward the distal end side, an engagement between the suture needle 204 and the first engaging member 205 is released, and the suture needle 204 may be dropped out of the first grasp member 210. In addition, there are cases in which the linear members 207 and 208 are buckled in the vicinity of the support pin 214 when the grasp portion 203 is widely opened. To resolve such a problem, providing a guide or the like for maintaining the path of the linear members 207 and 208 at a suitable position may be considered, but it is not preferable because the device becomes larger.

In contrast, in the suturing device 1 according to the present embodiment, the first linear member 7 is exposed from the lumen 10b of the first grasp member 10 to the proximal side, passes an outer side (an upper side in FIG. 3) of the support pin 14, gently curves toward the joint pin, extends on an extension line on the proximal end side of the second grasp member 11, passes an outer peripheral side (a lower side in FIG. 3) of the joint pin (the proximal end side joint pin 16), and then, is inserted into the insertion path 21.

A portion on the proximal end side of the intersecting portion of the linear members 7 and 8 is inserted through the insertion path 21 substantially in parallel with the direction of the central axis L. As a result of disposing the linear members 7 and 8 as above, in a state in which the grasp portion 3 is closed, the linear members 7 and 8 are spaced apart with respect to the central axis L by coming into contact with the support pin 14 and are restricted so that the intersecting position of the first linear member 7 and the second linear member 8 in the direction of the central axis L is on the proximal end side with respect to the support pin 14.

At the time of use, the linear members 7 and 8 are disposed to intersect the central axis L on a further distal side with respect to the distal end of the sheath 22 into which the longitudinal axis member 2 is inserted. On the proximal side with respect to the intersecting portion of the linear members 7 and 8, the linear members 7 and 8 are inserted into the sheath 22 such that each of their positions with respect to the central axis L is restricted. As a result, the path of the linear members 7 and 8 on the proximal side with respect to the intersecting portion are capable of being easily restricted to a desired position, and the curving motion or the advancing and retracting motion of the linear members 7 and 8 are capable of being maintained in an appropriate state.

Since the ring member 19a is enclosed in the sheath 22, it is possible to prevent the suture thread 18 or the tissue from interfering with the ring member 19a and hindering a movement of the ring member 19a.

In the suturing device 1 according to the present embodiment, since the linear members 7 and 8 are disposed to intersect the central axis L of the longitudinal axis member 2, the linear members 7 and 8 are not straight but are curved to some extent even when the grasp portion 3 is in a closed state. Therefore, the linear members 7 and 8 are capable of being smoothly curved at the time of the opening motion of the grasp portion 3. In addition, it is possible to secure a large curvature of the curved portion of the linear members 7 and 8 at the time of the opening motion of the grasp portion 3. Specifically, at the time of the opening motion of the grasp portion 3, the curvature of the curve of the linear members 7 and 8 hardly changes and only an angle of the curve changes by a predetermined amount. That is, at the time of the opening operation of the grasp portion 3, the path on the proximal side from a curved center of the linear members 7 and 8 does not change while the path on the distal side from the curved center rotates around the curved center in accordance with the rotation of the grasp members 10 and 11. Therefore, the grasp portion 3 is capable of being opened and closed without changing the distal end positions of the linear members 7 and 8 with respect to the grasp members 10 and 11. As a result, at the time of the opening motion of the grasp portion 3, the linear members 7 and 8 are smoothly curved and it is possible to prevent buckling or dropping of the suture needle as described above. In an endoscope treatment tool in which a treatment tool with a small diameter is desired, a smooth operation is capable of being be realized by disposing the linear member in a path by which a sufficient radius of curvature is capable of being secured without greatly changing the diameter dimension.

Since the position at which the linear members 7 and 8 intersect the central axis L of the longitudinal axis member 2 is set on the proximal end side with respect to a supporting point of the opening and closing operation of the pair of grasp members 10 and 11, even when the pair of grasp members 10 and 11 are widely opened, the linear members 7 and 8 are not excessively curved and occurrence of buckling is capable of being suppressed.

Since the linear members 7 and 8 are inserted into a gap formed in the link member 12 attached to conventional grasp forceps, the suturing device 1 according to the present embodiment is capable of achieving both of securing a sufficient radius of curvature of the linear members 7 and 8 and saving space and is capable of providing a suturing device excellent in operability.

The intersection point of the first linear member 7 and the second linear member 8 when viewed from the axial direction of the support pin 14 is between the support pin 14 of the grasp portion 3 and the proximal end side joint pin 16 in the direction of the central axis L. Therefore, in a state in which the grasp portion 3 is opened, the curve positions of the first linear member 7 and the second linear member 8 are restricted by coming into contact with the proximal end side joint pin 16. As a result, functions of the linear members 7 and 8 are not easily affected by the opening motion of the grasp portion 3.

In the present embodiment, a case in which the grasp members 10 and 11 and the longitudinal axis member 2 are connected with the link member 12 interposed therebetween is given as an example. However, since the grasp members have only to be configured to be connected to a longitudinal axis member to be openable and closeable, for example, there may be a configuration in which grasp members and a longitudinal axis member are connected using a cam slot.

In the present embodiment, an example in which the engagement of the engaging members 5 and 6 and the suture needle 4 is maintained by pulling the engaging members 5 and 6 toward the proximal side has been illustrated. However, the present suturing device eliminates a problem caused by a large change in the path of the linear member accompanying the opening and closing operation of the grasp members 10 and 11, and, for example, a configuration in which the engagement of the engaging member and suture needle is maintained by pushing the engaging member to the distal side is also capable of being applied. That is, even in the case of a method in which the engagement of the suture needle and the engaging member is maintained by advancing the engaging member to the distal side, the opening and closing of the grasp portion 3 hardly affect the path of the linear member and it is possible to prevent the linear member from buckling by suppressing an increase in compressive stress on the linear member.

In the present embodiment, the suture needle 4 is configured to have the pointed end portion 4a on the distal end side and the flange portion 4d on the proximal end side, but a shape of the suture needle is not limited thereto, and it may be configured to have a pointed end portion at both the distal end portion and the proximal end portion, for example.

In addition to the above configuration, the transfer operation unit of the present embodiment may have a configuration in which a tension spring is connected between the proximal end portion of the linear member and the handle which is provided in the operation unit main body.

Second Embodiment

Next, a suturing device 1A of a second embodiment of the present invention will be described with reference to FIG. 11. A difference between the present embodiment and the first embodiment is a configuration of a link member. In the following description, components the same as those already described are denoted by the same reference signs and duplicated descriptions thereof will be omitted.

Figure 11:
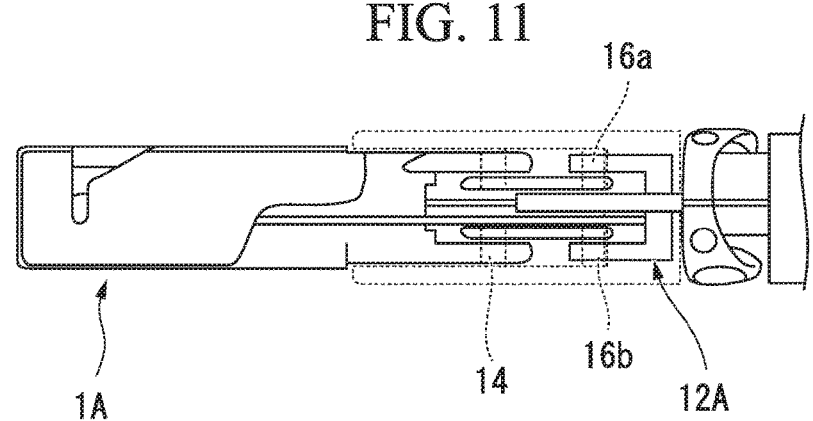
FIG. 11 is a partial cross-sectional view illustrating a distal end portion of a suturing device according to a second embodiment of the present invention.

FIG. 11 is a partial cross-sectional view illustrating a distal end portion of the suturing device 1A. Two proximal end side joint pins of a link member 12A are provided in the suturing device 1A according to the present embodiment. That is, the link member 12A includes a first proximal end side joint pin (a first joint pin) 16a and a second proximal end side joint pin (a second joint pin) 16b. The first proximal end side joint pin 16a connects a first grasp member 10 with a longitudinal axis member 2. The second proximal end side joint pin 16b is provided to be spaced apart from the first proximal end side joint pin 16a on the same axis as the first proximal end side joint pin 16a. The second proximal end side joint pin 16b connects a second grasp member 11 with the longitudinal axis member 2. Since the two proximal end side joint pins 16a and 16b are disposed on the same axis, a motion of the link member 12 is the same as in the first embodiment. That is, when each proximal end portion of a pair of link members 12 is connected to a distal end of the longitudinal axis member 2, each proximal end portion of the pair of link members 12 is respectively connected to different proximal end side joint pins 16a and 16b. In this manner, a gap between the two proximal end side joint pins 16a and 16b is capable of being formed while maintaining a function of the link member by having two separate proximal end side joint pins in a rotating axis direction. Linear members 7 and 8 are disposed in the gap between the proximal end side joint pins 16a and 16b.

According to the present embodiment, the linear members 7 and 8 that perform a transfer motion of a suture needle 4 are hardly affected by an opening and closing operation of a grasp portion and a stable suturing treatment is capable of being performed.

According to the present embodiment, the linear members 7 and 8 can be disposed in the gap between the two proximal end side joint pins 16a and 16b. Therefore, it is possible to secure a place for disposing the linear members 7 and 8 in a treatment tool that is desired to be reduced in diameter. Further, wirings of the linear members 7 and 8 extending from the distal end of the longitudinal axis member 2 are not disturbed by the proximal end side joint pins.

While embodiments of the present invention have been described in detail as above with reference to the accompanying drawings, the specific configurations are not limited to the embodiments but may include design changes without departing from the spirit of the present invention.

Moreover, the components represented in each of the embodiments and modifications thereto are capable of being configured by an appropriate combination thereof.

What is claimed is:

1. A suturing device, comprising:
a longitudinal axis member in which an insertion path extending in a longitudinal direction from a proximal end portion to a distal end portion is formed;
an operation unit provided on a proximal end portion side of the longitudinal axis member;
a grasp portion provided on a distal end portion side of the longitudinal axis member and configured to be capable of performing an opening and closing motion of a pair of grasp members by using an opening-closing operation member, the pair of grasp members including a first grasp member and a second grasp member;
a suture needle having an engaging portion engageable with the pair of grasp members;
a first engaging member provided in the first grasp member and configured to engage the suture needle with the first grasp member by engaging with the engaging portion;
a second engaging member provided in the second grasp member and configured to engage the suture needle with the second grasp member by engaging with the engaging portion;
a first linear member connected to the first engaging member and the operation unit and configured to switch the first engaging member and the engaging portion into an engaged state or a disengaged state by moving in the longitudinal direction; and
a second linear member connected to the second engaging member and the operation unit and configured to switch the second engaging member and the engaging portion into an engaged state or a disengaged state by moving in the longitudinal direction,
wherein the first linear member and the second linear member are inserted into the insertion path in a state in which the first linear member and the second linear member intersect a central axis of the longitudinal axis member at a proximal side with respect to a rotating shaft portion of the pair of grasp members.

2. The suturing device according to claim 1,
wherein the first engaging member is provided in the first grasp member to be slidable along a surface facing the second grasp members,
the second engaging member is provided in the second grasp member to be slidable along facing a surface facing the first grasp members, and
the first engaging member and the second engaging member respectively slide with respect to the first grasp member and the second grasp member by advancing and retracting the first linear member and the second linear member, thereby one of the first engaging member and the second engaging member is engaged with the engaging portion and the suture needle is held by one of the pair of grasp members corresponding to an engaging member engaged with the engaging portion.

3. The suturing device according to claim 2,
wherein the first engaging member and the second engaging member are configured to be engaged with the engaging portion by sliding toward each proximal side of the grasp members.

4. The suturing device according to claim 1, further comprising:
a cover member which fixes a rotating shaft portion of the pair of grasp members to the longitudinal axis member; and
a pair of link members in which a distal end side thereof is connected to the rotating shaft portion and a proximal end side thereof is connected to a distal end portion of the opening-closing operation member,
wherein the pair of grasp members open and close via the link members by advancing and retracting the opening-closing operation member with respect to the longitudinal axis member; and
the first linear member and the second linear member pass between the pair of link members and intersect with each other on the proximal side with respect to the rotating shaft portion.

5. The suturing device according to claim 4,
wherein, in a state in which the pair of grasp members are closed,
the first linear member and the second linear member come into contact with the rotating shaft portion such that the first linear member and the second linear member is spaced apart with respect to the central axis and an intersecting position of the first linear member and the second linear member in the longitudinal direction is restricted to be on a proximal side with respect to the rotating shaft portion.

6. The suturing device according to claim 4, wherein:
the first linear member and the second linear member intersect between the rotating shaft portion of the pair of grasp members and a link rotating shaft portion of the link members in the longitudinal direction; and
in a state in which the pair of grasp members are opened, the first linear member and the second linear member come into contact with the link rotating shaft portion such that a curved position is restricted.

7. The suturing device according to claim 4,
wherein the link members include:
a first joint pin which connects the first grasp member with the longitudinal axis member; and
a second joint pin provided to be spaced apart from the first joint pin on a same axis as the first joint pin and configured to connect the second grasp member with the longitudinal axis member,
wherein the first linear member and the second linear member are inserted into a distal end portion of the longitudinal axis member through a gap between the first joint pin and the second joint pin.

8. The suturing device according to claim 1,
wherein the first linear member and the second linear member are provided to extend at positions spaced apart with the central axis interposed therebetween when viewed from an opening and closing direction of the pair of grasp members.

9. The suturing device according to claim 1, further comprising:
a sheath into which the longitudinal axis member is inserted; and
a switching mechanism disposed in the sheath with the longitudinal axis member, connected to the first linear member and the second linear member, and configured to alternatively switch the engaged state or the disengaged state of the engaging portion with the first engaging member and the second engaging member.

* * * * *